United States Patent [19]

Verkade et al.

[11] Patent Number: 5,698,737
[45] Date of Patent: Dec. 16, 1997

[54] PROPHOSPHATRANE DEPROTONATION OF SOLVENTS

[75] Inventors: John G. Verkade, Ames, Iowa; Thyagarajan Mohan, Tamil Nadu, India; Andrzej E. Wróblewski, Zamenhofa, Poland

[73] Assignee: Iowa State University Research Foundation, Ames, Iowa

[21] Appl. No.: 477,760

[22] Filed: Jun. 7, 1995

[51] Int. Cl.$^6$ .................. C07F 9/02; C07F 9/547
[52] U.S. Cl. .................................. 564/13; 564/12
[58] Field of Search ........................ 564/12, 13

[56] References Cited

U.S. PATENT DOCUMENTS 5,051,533  9/1991  Verkade et al. .............. 564/13
5,260,436  11/1993  Verkade et al. .............. 544/193

OTHER PUBLICATIONS

L.E. Carpenter et al., "An Ivestigation of the Mode of Formation of the 10-P-5 Protonated Phosphatrane $HP(OCH_2CH_2)_3N^{+}$", J. Org. Chem., 51, 4287-4288 (1986).
P.G. Chantrell et al., "Preparation of Some Novel Diphosphorus Compounds. I. 1,4-Phenylene-Diphosphorus Compounds", J. Appl. Chem., 14, 563-564 (Dec. 1964).
S.K. Das et al., "Electronic and Structural Aspects of Rectangular Pyramidal Hypervalent 10-P-5 Compounds", Phosphorus and Sulfur, 30, 301-304 (1987).
R.J. Garant et al., "Lewis Basicity of Silatranes and the Molecular Structures of $EtOSi(OCH_2CH_2)_3N$, $Me_2O^+Si(OCH_2CH_2)N$, and $CF_3CO_2HEtOSi(OCH_2CH_2)_3N^+$", J. Am. Chem. Soc., 113, 5728-5735 (1991).
D. Gudat et al., "Novel Properties of New Phosphatranes and Silatranes", Phosphorus, Sulfur and Silica, 41, 21-29 (1989).
D. Gudat et al., "New Azasilatranes: Sterically Induced Transannular Bond Weakening and Cleavage", J. Am. Chem. Soc., 111, 8520-8522 (1989).
D. Gudat et al., "New Azasilatranes: Synthesis and Substitution Reactions", Organometallics, 8, 2772-2779 (1989).
D. Gudat et al., "New Azasilatranes: Bidentate and Tridentate Coordination Modes of the Novel Ligand $EtOSi(Ph_2PNCH_2CH_2)_2(HNCH_2CH_2)N$", Organometallics, 9, 1464-1470 (1990).
D. Gudat et al., "Azasilatrane Methanolysis Pathways: Stereoelectronic Influences", Organometallics, 9, 2172-2175 (1990).
M.A.H. Laramay et al., "The 'Anomalous' Basicity of $P(NHCH_2CH_2)_3N$ Relative to $P(NMeCH_2CH_2)_3N$ and $P(NBzCH_2CH_2)_3N$: A Chemical Consequence of Orbital Charge Balance?", J. Am. Chem. Soc., 112, 9421-9422 (1990).
M.A.H. Laramay et al., "Unusually Lewis Basic Pro-azaphosphatranes,", Z. Anorg. Allg. Chem., 605, 163-174 (1991).
C. Lensink, et al., "The Unusually Robust P-H Bond in the Novel Cation $HP(NME CH_2CH_2)_3N^{+}$" J. Am. Chem. Soc., 111, 3478-3479 (1989).

D.S. Milbrath et al., "Bicyclic and Tricyclic Phosphatranes. Conditions for Transannular P←N Bonding in a New Class of Phosphorus Cage Compounds," J. Am. Chem. Soc., 99, 6607-6613 (Sep. 28, 1977).
H. Oediger et al., "A new reagent for the introduction of double bonds", Chemische Berichte, 99, 2012-2016 (1966).
T. Pietzonka et al., "Alkylations of (R,R)-2-t-Butyl-6-methyl-1,3-dioxan-4-ones which are not Possible with Lithium Amides may be Achieved with a Schwesinger P4 Base", Chem. Ber., 124, 1837-1843 (1991).
J. Pinkas et al., "Group 13 Azatranes: Synthetic, Conformational and Configurational Features", J. Am. Chem. Soc., 115, 3925-3931 (1993).
H. Schmidt et al., "New Prophosphatranes: Novel Intermediates to Five-Coordinate Phosphatranes", Z. anorg. allg. Chem., 578, 75-80 (1989).
H. Schmidt et al., "Azaphosphatranes and Pro-Azaphosphatranes", Phosphorus, Sulfur and Silicon, 49/50, 163-168 (1990).
R. Schwesinger, "Extremely Strong, Non-ionic Bases: Syntheses and Applications", Chimia, 39, 269-272 (Sep. 1985).
R. Schwesinger et al., "Peralkylated Polyaminophosphazenes -Extremely Strong, Neutral Nitrogen Bases", Angew. Chem. Int. Ed. Engl., 26, 1167-1169 (1987).
J.-S. Tang et al., "Stepwise Transannular Bond Formation between the Bridgehead Atoms in $ZP(MeNCH_2CH_2)_3N$ Systems", J. Am. Chem. Soc., 114, 3129-3131 (1992).
J.-S. Tang et al., "An Improved Synthesis of the Strong Base $P(MeNCH_2CH_2)_2N$", Tetrahedron Letters, 34, 2903-2904 (1993).
J.S. Tang et al., "Synthesis and Reactivity Patterns of New Proazaphosphatranes and Quasi-azaphosphatranes $ZP(MeNCH_2CH_2)_3N$", J. Am. Chem. Soc., 115, 1660-1664 (1993).
J.S. Tang et al., "$P(MeNCH_2CH_2)_3N$ as a Superior Catalyst in the Conversion of Isocyanates to Isocyanurates", Angew. Chem. Int. Ed. Engl., 32, 896-898 (1993).

(List continued on next page.)

Primary Examiner—Marianne M. Cintins
Assistant Examiner—Dwayne C. Jones
Attorney, Agent, or Firm—Mueting, Raasch Gebhardt & Schwappach

[57] ABSTRACT

A method is disclosed for deprotonating a compound comprising treating the compound with a base of the general formula:

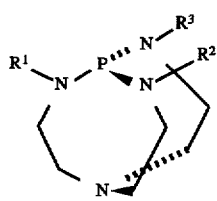

in the presence of a nitrile solvent; wherein $R^1$, $R^2$ and $R^3$ are each individually H, $(C_1-C_{15})$alkyl, $(C_6-C_9)$aryl, $(C_1-C_4)$alkyl$(C_6-C_9)$aryl, $((C_1-C_4)$alkyl$)_3$Si, or $(C_6-C_9)$aryl$(C_1-C_4)$alkyl.

12 Claims, No Drawings

OTHER PUBLICATIONS

J.S. Tang et al., "Synthesis of New Exceedingly Stong Non–Ionic Bases: RN=P(MeNCH$_2$CH$_2$)$_3$N", *J. Am. Chem. Soc.*, 115, 5015–5020 (1993).

J.S. Tang et al., "Chemical and Structural Implications of Bond Formation Between the Bridgehead Atoms in ZP(MeNCH$_2$CH$_2$)$_3$N Systems", *Phosphorus, Sulfur and Silicon*, 75, 205–208 (1993).

J.G. Verkade, "Ligation of Trivalent Phosphorus to Protons, Selenium and Metals: Some New Aspects", *Pure and Applied Chemistry*, 52, 1131–1139 (1980).

P. Mosset et al., "Trimethylsulfonium Methylsulfate, A Simple and Efficient Epoxidizing Agent", *Synthesis Communications*, 15, 749–757 (1985).

J.G. Verkade, "Five–Coordinate and Quasi–Five–Coordinate Phosphorus" in *ACS Symposium Series, Phosphorus Chemisytry*; E.N. Walsh et al., Eds.; American Chemical Society: Washington, DC; Chap. 5, pp. 64–75 (1992).

J.G. Verkade, "Atranes: New Examples with Unexpected Properties", *Acc. Chem. Res.*, 26, 483–489 (1993).

J. Woning et al., "New Azasilatrane Cations: Quaternization of an Equatorial Nitrogen in Azasilatranes", *J. Am. Chem. Soc.*, 113, 944–949 (1991).

J. Woning et al., "New Azasilatranes: Thermal Conversion of Unusual Azasilatranium Pseudohalides to Neutral 1–(Pseudohalogeno)azasilatranes", *Organometallics*, 10, 2259–2266 (1991).

S.K. Xi et al., "Bridgehead–Bridgehead Communication in Untrasannulated ZP(ECH$_2$CH$_2$)$_3$N Systems", *Inorg. Chem.*, 29, 2214–2220 (1990).

A. Zwierzak et al., "Synthesis of N,N,N',N'–Tetra–alkyl Phosphorodiamidites (R$_2$N)$_2$P(O)H", *Bulletin De L'Academie Polonaise Des Sciences*, XIII, 609–613 (1965).

Laramay et al., "Unusually Lewis Basic Pro–azaphosphatranes", *Z. Anorg. Allg. Chem.*, 605, 163–174, (1991).

Tang et al., "[P(MeNCH2CH2)3N] as a Superior Catalyst for the Conversion of Isocyanates to Isocyanurates", *Angew. Chem. Int. Ed. Engl.*, 32, 896–898 (1993).

PROPHOSPHATRANE DEPROTONATION OF SOLVENTS

This invention was made with support of the U.S. Department of Commerce under Grant No. ITA 87-02. The U.S. Government has certain rights in the invention.

BACKGROUND OF THE INVENTION

Strong non-ionic bases play an important role in organic synthesis because of the milder reaction conditions they generally permit, the enhanced reactivity of the more naked anions in the poorly associated ion pairs formed upon substrate deprotonation by such bases (in contrast to ionic bases), and the better solubility of non-ionic bases in organic solvents at or below room temperature, as required by some reactions. See, for example, R. Schwesinger, *Chimia*, 39, 269 (1985); T. Pietzonka et at., *Chem. Ber.*, 124, 1837 (1991); and R. Schwesinger et at., *Angew. Chem. Int. Ed. Eng.*, 26, 1167 (1987).

Reagents which are known to be useful for abstracting a proton from a wide variety of organic, organometallic, or inorganic substrates are commercially available. An ideal proton abstractor has the capability of abstracting protons from molecules reluctant to release protons and of holding the abstracted proton tightly. It is preferable, for ease of processing in complex organic syntheses, that once the proton abstractor has abstracted a proton, that it not induce unwanted side reactions and that it be easily separable as a stable product from the remaining portion of the reactants.

Commercially available strong bases, such as 1,8-diazabicyclo[5.4.0]undec-7-ene (DBU) and 1,5-diazabicyclo[4.3.0]non-5-ene (DBN) (Aldrich Chemical Company), the structures of which are shown below, are known in the art and are useful as proton abstracting reagents.

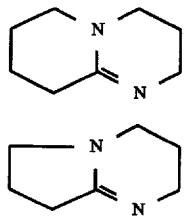

The synthesis of trans Vitamin A and its various isomers has been accomplished using bases such as DBN. See, for example, Oediger, H. et at., *Chem. Ber.*, vol. 99, p. 2012 (1966).

The proazaphosphatrane $P(MeNCH_2CH_2)_3N$ (1) is an even stronger non-ionic base (or "superbase") than the above examples and is also useful as a catalyst for the conversion of isocyanates to industrially important isocyanurates.

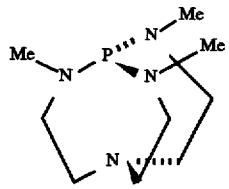

See, for example, J. Verkade et at., (U.S. Pat. No. 5,260, 436); J. Verkade, (U.S. Pat. No. 5,051,533); and H. Schmidt et at., *Z. Anorg. Allg. Chem.*, 578, 75 (1990). The prophosphatrane P(MeNCH2CH2)3N, however, is a large, bulky molecule. It, therefore, can fail to extract a proton from a molecule in which the proton to be abstracted is hindered by nearby substituents. Proton abstraction has been especially problematic for certain precursor molecules to Vitamin A, because they present steric hindrance difficulties.

Thus, a need exists for a more efficient chemical process that facilitates proton abstraction from large substrate compounds which, due to their molecular structures, sterically hinder access of "superbases" to protons.

SUMMARY OF THE INVENTION

The present invention provides a method for deprotonating a compound comprising treating the compound with a base of the formula:

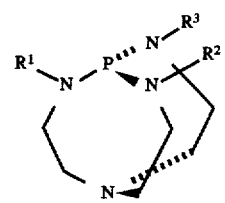

in the presence of a nitrile solvent; wherein $R^1$, $R^2$ and $R^3$ are each independently substituents that are nonreactive under conditions of the reaction. Preferably, $R'$, $R^2$ and $R^3$ are each individually H, $(C_1-C_{15})$alkyl, $(C_6-C_9)$aryl, $(C_1-C_4)$alkyl$(C_6-C_9)$aryl, $((C_1-C_4)$alkyl$)_3$Si, or $(C_6-C_9)$aryl$(C_1-C_4)$alkyl. More preferably, $R^1$, $R^2$ and $R^3$ are each individually H, $(C_1-C_4)$alkyl, $(C_6-C_9)$aryl, or $(alk)_3$Si wherein each alk is $(C_1-C_4)$alkyl. Of these, $R^1$, $R^2$ and $R^3$ are preferably each individually hydrogen or $(C_1-C_8)$alkyl (more preferably, hydrogen or $(C_1-C_4)$alkyl, and most preferably, hydrogen or methyl).

The compound to be deprotonated by the method of the present invention can be a bulky molecule such as a Vitamin A precursor. For example, the compound can be (2Z,4E, 8E)-6-bromo-3,7-dimethyl-9-(2,6,6-trimethyl-1-cyclohexen-1-yl)-2,4,8-nonatrien-1-yl acetate or (3E,5E,8E)-2-bromo-3,7-dimethyl-9-(2,6,6-trimethyl-1-cyclohen-1-yl)-3,5,8-nonatrien-1-yl acetate.

The nitrile solvent of the present invention preferably is of the formula $R^4R^5CHCN$, wherein $R^4$ and $R^5$ are each individually hydrogen; saturated or unsaturated, substituted or unsubstituted linear $(C_1-C_8)$alkyl; or substituted or unsubstituted $(C_6-C_4)$aryl. More preferably, $R^4$ and $R^5$ are each hydrogen. Most preferably, the nitrile solvent is acetonitrile.

DETAILED DESCRIPTION OF THE INVENTION

It has been discovered that nitriles, such as acetonitrile $(CH_3CN)$, when used in conjunction with, for example, the superbase $P(MeNCH_2CH_2)_3N$, produce a small, potent base (e.g., $^-CH_2CN$) which effectively deprotonates larger substrate molecules. It was previously observed that the proazaphosphatrane $P(MeNCH_2CH_2)_3N$ was not efficient at deprotonating the precursor bromide (3) to Vitamin A.

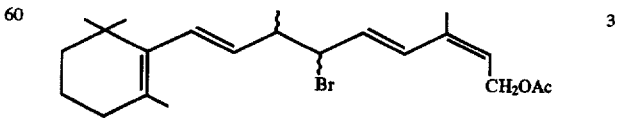

The combination of this superbase with nitriles, such as acetonitrile, however, is surprisingly effective in deprotonating large, bulky molecules such as compound 3. Further, the combination of a phosphatrane and a nitrile in accordance with this invention unexpectedly allows the deprotonating reaction to take place at room temperature (i.e., 25°–30° C.).

The reaction of the present method is summarized in reaction Scheme I below:

Scheme I

P(RNCH₂CH₂)₃N + HCR₂CN ⟶

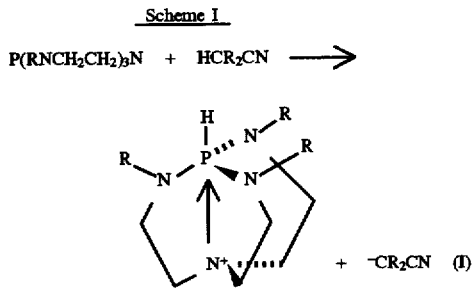

+ ⁻CR₂CN  (I)

wherein a group R is a substituent which is nonreactive under conditions of the reaction. Herein when it is said that a group R (for example $R^1$, $R^2$ and $R^3$) is nonreactive under the reaction conditions it is meant that the group R is such that it does not participate in the reaction and it does not undergo chemical change or transformation during the reaction. The R groups should also be such that they do not prevent the reaction. Herein when it is said that an R group (for example $R^1$, $R^2$ and $R^3$) should be chosen such that it does not "prevent" reaction, it is meant that the group is selected such that the reactants can react in the manner described. For example, the R groups are chosen such that they do not provide sufficient steric hindrance for nonreactivity, nor do they prevent sufficient solubility for reaction. Herein guidance with respect to "nonreactive" R groups and R groups that do not "prevent" reaction is provided in each instance by representative groups. It is not meant, however, that the lists are exclusive.

According to the method of the invention, a target compound to be deprotonated is treated with a strong base in the presence of a nitrile solvent. The strong base is preferably a non-ionic prophosphatrane base according to the general formula (compound 2):

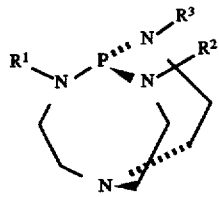 2 also sometimes referred to as "superbase." $R^1$, $R^2$ and $R^3$ are preferably each individually H, $(C_1-C_{15})$alkyl, $(C_6-C_9)$aryl, $(C_1-C_4)$alkyl$(C_6-C_9)$aryl, $[(C_1-C_4)$alkyl$]_3$Si, or $(C_6-C_9)$aryl$(C_1-C_4)$alkyl. More preferably, $R^1$, $R^2$ and $R^3$ are each individually H, $(C_1-C_9)$alkyl, $(C_6-C_9)$aryl, or (alk)$_3$Si wherein each alk is $(C_1-C_4)$alkyl. Of these, $R^1$, $R^2$ and $R^3$ are preferably each independently selected from the group consisting of hydrogen and $(C_1-C_8)$alkyl. It is even more preferred that $R^1$, $R^2$ and $R^3$ are selected from the group consisting of hydrogen and $(C_1-C_4)$alkyl. Most preferably, $R^1$, $R^2$ and $R^3$ are hydrogen or methyl. As used herein "individually" or "independently" mean that the R groups can be the same or different. A particularly preferred base, according to the method of the invention, is trimethyltriazaprophosphatrane, P(MeNCH₂CH₂)₃N (1).

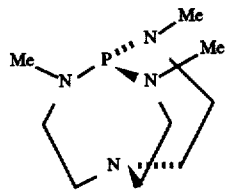 1

Synthesis of preferred bases according to the present invention is generally described in U.S. Pat. No. 5,051,533, the disclosure of which is incorporated herein by reference. Briefly, as shown in Scheme II below, the synthesis of 1 can be accomplished using ClP(NMe₂)₂ and tris-(betamethylaminoethyl)amine (trimethyl-TREN).

Scheme II

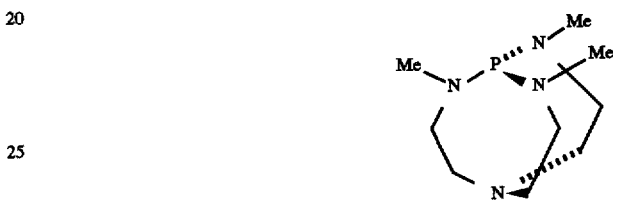

The prophosphatrane can be prepared as the hydrochloride by adding a solution of (HMeNCH₂CH₂)₃N in CH₂Cl₂ over a period of five minutes to a stirred solution of ClP(NMe₂)₂ in CH₂Cl₂. Stirring is continued at room temperature for one hour followed by removal of the solvent to afford the phosphatranyl chloride. The salt is recrystallized from hexane/chloroform at −20° C. The product is converted to the corresponding prophosphatrane by adding the salt dissolved in acetonitrile to a suspension of potassium tertiary butoxide in acetonitrile. The solvent is removed under vacuum and the residue extracted with hexanes. The residue is purified by vacuum sublimation to give the prophosphatrane.

An improved and preferred synthesis of base 1 is described in Verkade et al., *Tetrahedron Lett.*, 34, 2903 (1993). Briefly, (HMeNCH₂CH₂)₃N is added to a stirred solution of ClP(NEt₂)₂ in dry CH₃CN. After stirring, the reaction mixture is transferred to a flask containing t-BuOK in dry CH₃CN. After stirring, the reaction mixture, the solvent is removed under vacuum and the residue is extracted with dry pentane. The extract is evaporated using a vacuum to give a white solid which is purified by vacuum sublimation giving spectroscopically pure proazaphosphatrane.

Nitrile solvents which can be used in accordance with the invention are of the general formula $R^4R^5$CHCN, where $R^4$ and $R^5$ are each independently selected from the group consisting of hydrogen; saturated or unsaturated, substituted or unsubstituted linear $(C_1-C_8)$alkyl; or substituted or unsubstituted $(C_6-C_{14})$aryl. Most preferably $R^4$ and $R^5$ are each hydrogen (i.e., acetonitrile).

As illustrated in the Examples, target compounds can be deprotonated by reacting the compound with a superbase P(RNCH₂CH₂)₃N in a nitrile solvent HCR₂CN with no criticality of temperature. Advantageously, the reaction can take place at room temperature, i.e., about 25°–30° C.

Reasonable modifications and variations are possible from the foregoing disclosure without departing from either the spirit or scope of the present invention as defined by the claims. Objects and advantages of this invention will now be illustrated by the following examples, but the particular materials and amounts thereof recited in these examples, as well as other conditions and details, should not be construed to unduly limit this invention.

EXPERIMENTAL EXAMPLES

Unless otherwise noted, materials were obtained from commercial suppliers and were used without purification. Solvents were reagent grade, pre-dried over molecular sieves, and when necessary, distilled from sodium-benzophenone ketyl prior to use (THF, ether). Removal of solvents from oily reaction products, was carried out by applying vacuum and magnetically stirring at room temperature until 20 mTorr was achieved. However, residual hexane was still present especially for viscous compounds as judged from their $^1$H NMR spectra. Efforts to remove hexane by heating under vacuum resulted in decomposition.

$^1$H NMR spectra were measured on Nicolet NT-300 and Varian VXR-300 NMR spectrometers in chloroformed while $^{13}$C and $^{31}$p NMR spectra were recorded on a Varian VXR-300 NMR spectrometer in chloroformed and acetonitrile-d$_3$, respectively. Chemical shifts are reported in ppm downfield from tetramethylsilane using chloroform ($^1$H, 7.23 ppm) and chloroform-d ($^{13}$C, 77.07 ppm) resonances as secondary standards. $^1$H and $^{13}$C chemical shift assignments were supported by 2D $^1$H–$^1$H correlations performed on 3 and 5 as a mixture, and mixtures of 6a and 6b, and by 2D $^1$H–$^{13}$C correlations recorded for 6a and 6b as a mixture (structures of these compounds are shown below). 2D spectra were obtained on a Varian VXR-300 spectrometer using standard COSY and HETCOR experiments.

For preparative chromatographic separations, silica gel (60–200 mesh, EM Science) was used, except for Vitamin A isomers, for which only deactivated alumina (neutral, Baker) was found useful. TLC analyses were performed using plates precoated with silica gel (IB-2 and IB-F) or alumina (IB-F) (both Baker-flex from Baker). The following solvent systems were employed: hexane-ethyl acetate, 3:1, v/v (for silica gel plates); and hexane-ethyl acetate, 10:1, v/v (for alumina plates). Trimethylsulfonium methylsulfate was prepared in 88% yield by the reaction of dimethylsulfate with dimethyl sulfide in acetone. P. Mosset et al., *Synthesis Communications*, 15, 749 (1985).

EXAMPLE 1

Reaction of Phosphorous Tribromide with 4 to Prepare Protonated Intermediate Compound To a solution of 10 mmol (2E,4E,6E,8E)-3,7-dimethyl-9-(2,6,6-trimethyl- 1-cyclohexen-1-yl)-2,4,6,8-nonatetraene-1-ol (4) in ether ( 10 ml), PBr3 (12 mmol) was injected at –20° C. under argon.

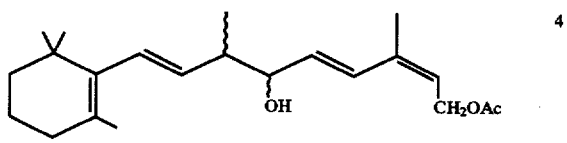

The reaction mixture was stirred for one hour which allowed it to reach room temperature. The mixture was then diluted with ether (40 ml) and sequentially washed with cold brine, aqueous NaHCO$_3$, and brine until neutral. Finally, the resulting product was dried over MgSO$_4$. After evaporation of ether, the crude product was left in vacuo (0.02 Torr) to give a mixture of the Vitamin A precursors (2Z, 4E, 8E)-6-bromo-3,7-dimethyl-9-(2,6,6-trimethyl-1-cyclohexen-1-yl)-2,4,8-nonatrien-1-yl acetate (two isomers 3a and 3b) and (3E,5E, 8E)-2-bromo-3,7-dimethyl-9-(2,6,6-trimethyl-1-cyclohen-1-yl)-3,5,8-nonatrien-1-yl acetate (5) as a yellow oil in 85–95% yield. Since this material slowly rams brown when left at room temperature, it was immediately used in the next step.

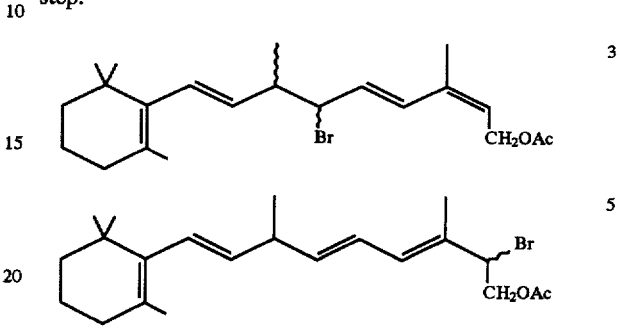

The following data were obtained from NMR spectroscopy of the resulting product:

3a: $^1$H NMR: δ 0.95 and 0.96 (2S, H$_3$C16,17), 1.16 (d, H3C19, J=6.8 Hz), 1.35–1.45 (m, H$_2$C2), 1.50–1.60 (m, H$_2$C3), 1.64 (bs, H$_3$C18), 1.84 (d, H$_3$C20, J=0.9 Hz), 1.93 (bt, H$_2$C4, J=6 Hz), 2.03 (s, CH$_3$CO), 2.55 (bsx, HC9, J=7 Hz), 4.59 (dd, HC10, J=10.2 Hz, J=5.0 Hz), 4.67 (d, H$_2$C15, J=7.3 Hz), 5.28 (dd, HCS, J=15.7 Hz, J=8.3 Hz), 5.51 (bt, HC14, J=7 Hz), 5.88 (bd, HC7, J=15.9 Hz), 5.96 (dd, HC11, J=15.4 Hz, J=10.2 Hz), 6.54 (d, HC12, J=15.3 Hz).

3b: $^1$H NMR: δ 0.92 and 0.93 (2S, H3C16,17), 1.18 (d, H$_3$C19, J=6.8 Hz), 1.35–1.45 (m, H$_2$C2), 1.50–1.60 (m, H$_2$C3), 1.59 (d, H$_3$C18, J=0.8), 1.83 (d, H$_3$C20, J=1.8 Hz), 1.92 (bt, H$_2$C4, J=6 Hz), 2.03 (s, CH$_3$CO), 2.65 (bsx, HC9, J=7 Hz), 4.53 (dd, HC10, J=10.2 Hz, J=6.7 Hz), 4.66 (d, H$_2$C15, J=7.2 Hz), 5.23 (dd, HC8, J=15.7 Hz, J=8.3 Hz), 5.49 (bt, HC14, J=7.2 Hz), 5.88 (bd, HC7, J=15.9 Hz), 5.91 (dd, HCl 1, J=15.3 Hz, J=10.2 Hz), 6.52 (d, HC12, J=15.3 Hz).

5: $^1$H NMR: δ 0.95 (s, H$_3$C16,17), 1.13 (d, H$_3$C19, J=7.0 Hz), 1.35–1.45 (m, H$_2$C2), 1.50–1.60 (m, H$_2$C3), 1.64 (bs, H$_3$C18), 1.80 (bs, H$_3$C20), 1.92 (bt, H$_2$C4), 2.01 (s, CH$_3$CO), 2.97 (bsx, HC9, S =7 Hz), 4.29 and 4.39 (AB part of ABX, H$_2$C15, J$_A$=11.7 Hz, J=8.1 Hz, J=7.0 Hz), 4.72 (dd≈t, HC14, J=8.1 Hz, J=7.0 Hz), 5.23 (dd, HC8, J=15.9 Hz, J=8.0 Hz), 5.78 (dd, HC10, J=13.8 Hz J=7.0 Hz), 5.82 (bd, HC7, J=16 Hz), 6.13 (AB, HC12, J$_{AB}$=10.9 Hz), 6.20 (ddAB, HC11, J$_{AB}$=10.9 Hz, J=13.8 Hz, J=1.0 Hz).

EXAMPLE 2

Removal of HBr from Mixtures of 3a, 3b and 5 with 1, DBN or DBU

A mixture of 3a, 3b and 5 obtained from Example 1 was dissolved in benzene or toluene (1 mmol in 1 ml) and refluxed with 1.2 equivalents of 1, DBN or DBU. The reaction mixture was diluted with ether and washed with brine until neutral. The crude products were then filtered through deactivated alumina (12 g for 5 mmol) to give mixtures of isomers 6a and 6b (major) and isomers 7a and 7b (minor).

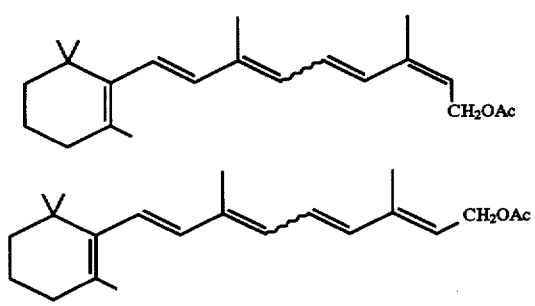

The following data were obtained from NMR spectroscopy of the resulting product:

6a: $^1$H NMR: δ 1.00 (s, H$_3$C16,17), 1.42–1.47 (m, H$_2$C2), 1.53–1.63 (m, H$_2$C3), 1.71 (d, H$_3$C18, J=0.7 Hz), 1.90 (d, H$_3$C20, J=0.9 Hz), 1.94 (bs, H$_3$C19), 2.01 (bt, H$_2$C4, J=6.2 Hz), 2.03 (s, CH$_3$CO), 4.71 (d, H$_2$C15, J=7.2 Hz), 5.45 (bt, H$_2$C14, J=7.2 Hz), 6.02 (d, HC10, J=11.3 Hz), 6.18 (d, HC7, J=15.9 Hz), 6.51 (d, HC12, J=15.0 Hz), 6.59 (d, HC8, J=15.9 Hz), 6.76 (dd, HC11a, J=15.0 Hz, J=11.3 Hz); $^{13}$C NMR: δ 19.18 (C3), 20.36 (H$_3$C20), 20.65 (H$_3$C19), 20.81 (CH$_3$CO), 21.72 (H$_3$C18), 28.88 (H$_3$C16,17), 32.92 (C4), 34.09 (C1), 39.42 (C2), 60.12 (C15), 122.51 (C14), 126.49 (C11), 127.17 (C12), 128.61 (C10), 128.85 (C7), 129.42 (C5), 129.69 (C8), 135.86 (C9), 137.91–138.03 (C6, C13), 170.73 (CO).

6b: $^1$H NMR: a 0.99 (s, H$_3$C16,17), 1.42–1.47 (m, H$_2$C2), 1.53–1.63 (m, H$_2$C3), 1.68 (d, H$_3$C18, J=0.6 Hz), 1.92 (d, H$_3$C20, J=1.0 Hz), 1.93 (d, H$_3$C19, J=0.7 Hz), 1.99 (bt, H$_2$C4, J=6.2 Hz), 2.03 (s, CH$_3$CO), 4.71 (bd, H$_2$C15, J=7.2 Hz), 5.45 (t, H$_2$C14, J=7.2 Hz), 6.09 (d, HC8, J=16.1 Hz), 6.11 (d, HC10, J=11.1 Hz), 6.17 (d, HC7, J=16.1 Hz), 6.57 (d, HC12, J=15.0 Hz), 6.67 (dd, HC11, J=15.0 Hz, J=11.1 Hz); $^{13}$C NMR: δ 12.64 (H$_3$C19), 19.18 (C3), 20.32 (H$_3$C20), 20.81 (CH$_3$CO), 21.62 (H$_3$C18), 28.85 (H$_3$C16, 17), 32.92 (C4), 34.13 (C1), 39.51 (C2), 60.12 (C15), 122.60 (C14), 127.22 (C7), 127.62 (C$_{10}$, 127.88 (C12), 129.30 (C5), 130.08 (C10), 137.13 (C9), 137.45 (C8), 137.64 (C13), 137.91–138.033 (C6), 170.69 (CO).

EXAMPLE 3

Removal of HBr from Mixtures of 6a, 6b and 7 with Acetonitrile and 1, DBN or DBU A mixture of 38, 3b and 5 obtained from Example 1 was dissolved in acetonitrile (1 mmol in 1 ml) and stirred at room temperature with 1.2 equivalents of 1, DBN or DBU. The reaction mixture was diluted with ether and washed with brine until neutral. The crude products were then filtered through deactivated alumina (12 g for 5 mmol) to give mixtures of isomers 68 and 6b (major) and isomers 78 and 7b (minor). The NMR spectroscopy data of the resulting products 6a and 6b (major) and the peaks seen for 78 and 7b (minor) were the same as for Example 2 above. The yields and stereochemical results of HBr elimination from the bromides 3 and 5 are given in Table 1 below.

TABLE I

Yields and Stereochemical Results of HBr Elimination from the Bromides 3 and 5

| Starting materials | | | | time, | Products | | |
|---|---|---|---|---|---|---|---|
| 3a:3b[a] | 5:(3a + 3b)[b] | Reagent | Solvent | min | 6a:6b[c] | 7:6[d] | Yield % |
| 75:25 | 9:91 | DBN | Benzene | 15 | 66:34 | 15:85 | —[e] |
| 40:60 | 30:70 | DBN | Benzene | 15 | 40:60 | 20:80 | —[e] |
| 31:69 | 23:77 | DBN | Benzene | 30 | 36:64 | 34:66 | 61[f] |
| 38:62 | 10:90 | DBN | Toluene | 15 | 42:58 | 23:77 | 50[f] |
| 31:69 | 23:77 | DBN | Acetonitrile | 60 | 36:64 | 24:76 | 61[f] |
| 31:60 | 23:77 | DBU | Acetonitrile | 60 | 37:63 | 30:70 | 63[f] |
| 35:65 | 20:80 | 1 | Acetonitrile | 60 | 37:63 | 18:82 | 49[f] |
| 31:69 | 23:77 | 1 | Acetonitrile | 60 | 36:64 | 22:78 | 52[f] |

[a]Based on relative intensities of H12 signals.
[b]Based on integrals of H9 signals.
[c]Based on integrals of H$_3$C18 signals.
[d]Based on integrals of H14 signals.
[e]Reaction proceeded to more than 95% completion.
[f]For isolated and purified products. For 1 there was substantially instantaneous and complete conversion.

P(CH$_3$NCH$_2$CH$_2$)$_3$N (1) was not effective removing hydrogen bromide from Vitamin A intermediates when the reaction was carried out in refluxing benzene. Data not shown.

The reaction of a prophosphatrane and acetonitrile with Vitamin A precursors 3 and 5 is depicted in Scheme III below:

Scheme III

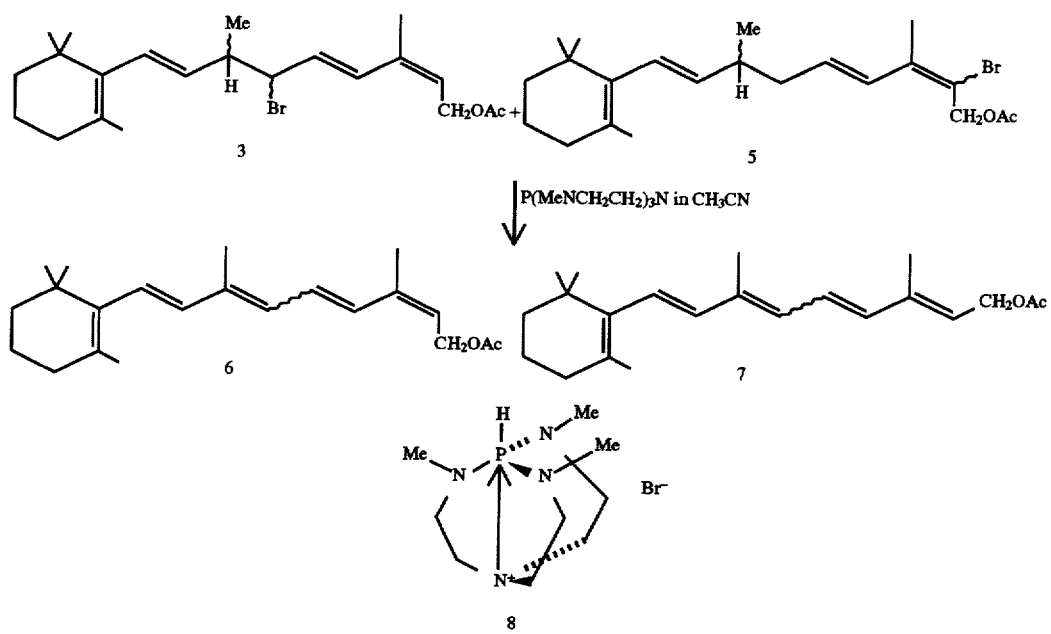

Dehydrobromination conversion rates were lower using 1 compared with DBN or DBU in refluxing benzene. This observation can be rationalized based on the greater steric bulk around the basic phosphorus center in 1 compared with DBN and DBU. This is especially true as positive charge is built up on 1 when it becomes protonated and transannulated to the trigonal bipyramidal cation 8.

The superiority of 1 in elfcoting HBr elimination from 3 and 5 in acetonitrile at room temperature over 1 in refluxing benzene results from the formation of $CH_2CN^-$ which then acts as a sterically small but powerful base. This conclusion is supported by alp NMR data of the elimination of hydrogen bromide from 3 and 5 with 1 in acetonitrile-$d_3$. Before addition of the bromides, the $^{31}P$ NMR spectrum of an acetonitrile-$d_3$ solution of 1 showed signals of 1 (singlet at 120.8 ppm) and of minute quantities of its deuteriated cation (three lines of equal intensity at −10.0 ppm). When the reaction was complete, a small excess of 1 was still present, while more than 80% of 1 was converted to its deuteriated form and less than 20% was found as the protonated species.

The complete disclosures of all patents, patent applications, and publications are incorporated herein by reference as if each were individually incorporated by reference. The invention has been described with reference to various specific and preferred embodiments and techniques. However, it should be understood that many variations and modifications may be made while remaining within the spirit and scope of the invention.

What is claimed is:

1. A method for deprotonating a compound comprising treating the compound with a proazaphosphatrane base in the presence of a nitrile solvent.

2. The method of claim 1 wherein the proazaphosphatrane base has the formula:

wherein $R^1$, $R^2$ and $R^3$ are each individually H, $(C_1-C_{15})$ alkyl, $(C_6-C_9)$aryl, $(C_1-C_4)$alkyl$(C_6-C_9)$aryl, $((C_1-C_4)$alkyl$)_3$Si, or $(C_6-C_9)$aryl$(C_1-C_4)$alkyl.

3. The method of claim 2 wherein $R^1$, $R^2$ and $R^3$ are each individually H, $(C_1-C_8)$alkyl, $(C_6-C_9)$aryl, or $(alk)_3$Si wherein each alk is $(C_1-C_4)$alkyl.

4. The method of claim 3 wherein $R^1$, $R^2$ and $R^3$ are each individually hydrogen or $(C_1-C_8)$alkyl.

5. The method of claim 4 wherein $R^1$, $R^2$ and $R^3$ are each individually hydrogen or $(C_1-C_4)$alkyl.

6. The method of claim 5 wherein $R^1$, $R^2$ and $R^3$ are each individually hydrogen or methyl.

7. The method of claim 1 wherein the compound is a Vitamin A precursor.

8. The method of claim 7 wherein the compound is selected from the group consisting of (2Z,4E, 8E)-6-bromo-3,7-dimethyl-9-(2,6,6-trimethyl-1-cyclohexen-1-yl)-2,4,8-nonatrien-1-yl acetate and (3E,5E,8E)-2-bromo-3,7-dimethyl-9-(2,6,6-trimethyl-1-cyclohen-1-yl)-3,5,8-nonatrien-1-yl acetate.

9. The method of claim 1 wherein the nitrile solvent is of the formula $R^4R^5CHCN$, wherein $R^4$ and $R^5$ are each individually hydrogen; saturated or unsaturated, substituted or unsubstituted linear $(C_1-C_8)$alkyl; or substituted or unsubstituted $(C_6-C_{14})$aryl.

10. The method of claim 9 wherein $R^4$ and $R^5$ are each hydrogen.

11. The method of claim 10 wherein the nitrile solvent is acetonitrile of the formula $CH_3CN$.

12. The method of claim 1 wherein the deprotonation is carried out at room temperature.

* * * * *

UNITED STATES PATENT AND TRADEMARK OFFICE
CERTIFICATE OF CORRECTION

PATENT NO.: 5,698,737
DATED: December 16, 1997
INVENTOR(S): Verkade et al.

It is certified that error appears in the above-identified patent and that said Letters Patent is hereby corrected as shown below:

Col. 1, line 5, delete "Grant" and insert --Contract--;

Col. 1, line 17, delete "et at." and insert --et al.--;

Col. 1, line 18, delete "et at." and insert --et al.--;

Col. 1, line 48, delete "et at." and insert --et al.--;

Col. 1, line 64, delete "et at." and insert --et al.--;

Col. 1, line 66, delete "et at." and insert --et al.--;

Col. 1, line 67, delete "P(MeNCH2CH2)3N" and insert --P(MeNCH$_2$CH$_2$)$_3$N--;

Col. 2, line 30, delete "(C$_1$-C$_4$)alkyl" and insert --(C$_1$-C$_8$)alkyl--;

Col. 2, line 46, delete "(C$_6$-C$_4$)aryl" and insert --(C$_6$-C$_{14}$)aryl--;

Col. 3, line 57, delete "(C$_1$-C$_9$)alkyl" and insert --(C$_1$-C$_8$)alkyl--;

Col. 5, line 21, delete "chloroformed" and insert --chloroform-$d$--;

UNITED STATES PATENT AND TRADEMARK OFFICE
CERTIFICATE OF CORRECTION
Page 2 of 4

PATENT NO.: 5,698,737
DATED: December 16, 1997
INVENTOR(S): Verkade et al.

It is certified that error appears in the above-identified patent and that said Letters Patent is hereby corrected as shown below:

Col. 5, line 22, delete "$^{31}$p NMR" and insert --$^{31}$P NMR--;

Col. 5, line 23, delete "chloroformed" and insert --chloroform-d--;

Col. 5, line 53, delete "trimethyl- 1-cyclohexen" and insert --trimethyl-1-cyclohexen--;

Col. 5, line 54, delete "( 10 ml)" and insert --(10 ml)--;

Col. 5, line 54, delete "PBr3" and insert --PBr$_3$--;

Col. 6, line 1, delete "(0.02 Tort)" and insert --(0.02 Torr)--;

Col. 6, line 7, delete "rams" and insert --turns--;

Col. 6, line 26, delete "(25, H$_3$C16,17)" and insert (2s, H$_3$C16,17)--;

Col. 6, line 27, delete "H3C19" and insert --H$_3$C19--;

Col. 6, line 31, delete "HCS" and insert --HC8--;

Col. 6, line 34, delete "(25, H3C16,17)" and insert --(2s, H$_3$C16,17)--;

Col. 6, line 42, delete "(dd, HCl 1," and insert --(dd, HC11--;

Col. 6, line 47, delete "S = 7 Hz" and insert --J = 7 Hz--;

Col. 6, line 48, delete "$J_A$=11.7" and insert --$J_{AB}$ = 11.7--;

UNITED STATES PATENT AND TRADEMARK OFFICE
CERTIFICATE OF CORRECTION

PATENT NO.: 5,698,737
DATED: December 16, 1997
INVENTOR(S): Verkade et al.

It is certified that error appears in the above-identified patent and that said Letters Patent is hereby corrected as shown below:

Col. 6, line 50, delete "13.8 Hz J=7.0" and insert --13.8 Hz, J = 7.0--;

Col. 6, line 51, delete "HC12, ,$J_{AB}$" and insert --HC12, $J_{AB}$--;

Col. 7, line 21, delete "(d, HCS," and insert --(d, HC8,--;

Col. 7, line 22, delete "(dd, HC11a" and insert --(dd, HC11--;
Col. 7, line 29, delete "a 0.99" and insert --δ 0.99--;

Col. 8, line 9, delete "127.62 ($C_{10}$," and insert --127.62 (C11),--;

Col. 8, line 19, delete "38, 3b" and insert --3a, 3b--;

Col. 8, line 25, delete "68 and 6b" and insert --6a and 6b--;

Col. 8, line 25, delete "78 and" and insert --7a and--;

Col. 8, line 27, delete "78 and 7b" and insert --7a and 7b--;

UNITED STATES PATENT AND TRADEMARK OFFICE
CERTIFICATE OF CORRECTION

PATENT NO. : 5,698,737
DATED : December 16, 1997
INVENTOR(S) : Verkade et al.

It is certified that error appears in the above-identified patent and that said Letters Patent is hereby corrected as shown below:

Col. 8, Table 1 (2nd entry), delete "30:70 DBN" and insert --30:70 DBU--;

Col. 8, line 56, delete "carded" and insert --carried--;

Col. 9, line 38, delete "elfcoting" and insert --effecting--; and

Col. 9, line 42, delete "alp NMR" and insert --$^{31}$P NMR--.

Signed and Sealed this

Eighth Day of June, 1999

Attest:

Q. TODD DICKINSON

*Attesting Officer*    *Acting Commissioner of Patents and Trademarks*